(12) United States Patent
Wright et al.

(10) Patent No.: US 10,883,977 B2
(45) Date of Patent: Jan. 5, 2021

(54) WHOLE BLOOD SEPARATION SAMPLING APPARATUS

(71) Applicant: Spot Bioscience, LLC, San Francisco, CA (US)

(72) Inventors: Jason Wright, Austin, TX (US); James Hill, Manor, TX (US)

(73) Assignee: Spot Bioscience, LLC, San Francisco, CA (US)

( * ) Notice: Subject to any disclaimer, the term of this patent is extended or adjusted under 35 U.S.C. 154(b) by 0 days.

(21) Appl. No.: 15/104,317

(22) PCT Filed: Dec. 20, 2014

(86) PCT No.: PCT/US2014/071763
§ 371 (c)(1),
(2) Date: Jun. 14, 2016

(87) PCT Pub. No.: WO2015/095853
PCT Pub. Date: Jun. 25, 2015

(65) Prior Publication Data
US 2016/0313298 A1 Oct. 27, 2016

Related U.S. Application Data

(60) Provisional application No. 61/919,526, filed on Dec. 20, 2013.

(51) Int. Cl.
*G01N 33/49* (2006.01)
*B01L 3/00* (2006.01)
*G01N 1/40* (2006.01)

(52) U.S. Cl.
CPC .......... *G01N 33/491* (2013.01); *B01L 3/502* (2013.01); *B01L 3/5023* (2013.01); *G01N 1/4077* (2013.01); *B01L 2300/0681* (2013.01); *B01L 2300/08* (2013.01); *B01L 2300/0803* (2013.01); *B01L 2300/0809* (2013.01); *G01N 2001/4088* (2013.01)

(58) Field of Classification Search
None
See application file for complete search history.

(56) References Cited

U.S. PATENT DOCUMENTS

| | | | |
|---|---|---|---|
| 3,996,935 A | 12/1976 | Banko | |
| 5,798,041 A * | 8/1998 | Zuk, Jr. | A61M 1/3627 210/435 |
| 6,036,659 A * | 3/2000 | Ray | B01L 3/5023 600/573 |
| 6,106,732 A | 8/2000 | Johnston et al. | |
| 6,299,842 B1 | 10/2001 | Kozak et al. | |
| 6,303,081 B1 | 10/2001 | Mink et al. | |
| 7,311,671 B2 | 12/2007 | Jung et al. | |
| 7,601,546 B2 | 10/2009 | Bayloff et al. | |
| 7,605,004 B2 | 10/2009 | Zhou | |
| 7,914,461 B2 | 3/2011 | Richard et al. | |
| 9,040,236 B2 | 5/2015 | Hill et al. | |
| 9,759,640 B2 | 9/2017 | Hill et al. | |
| 2003/0032196 A1 | 2/2003 | Zhou | |
| 2004/0097829 A1 | 5/2004 | McRury et al. | |
| 2004/0161788 A1 | 8/2004 | Chen et al. | |
| 2005/0130310 A1 | 6/2005 | Wandell et al. | |
| 2006/0018799 A1 | 1/2006 | Wong et al. | |
| 2006/0184065 A1 | 8/2006 | Desmukh et al. | |
| 2007/0173741 A1 | 7/2007 | Deshmukh et al. | |
| 2008/0035568 A1 * | 2/2008 | Huang | B01D 63/02 210/646 |
| 2008/0114225 A1 | 5/2008 | Rabinovitz | |
| 2008/0220461 A1 | 9/2008 | Kuriger | |
| 2008/0286150 A1 | 11/2008 | Pankow | |
| 2009/0247902 A1 | 10/2009 | Reichert et al. | |
| 2010/0174211 A1 | 7/2010 | Frey et al. | |
| 2011/0077554 A1 | 3/2011 | Roe et al. | |
| 2011/0282238 A1 | 11/2011 | Houser et al. | |
| 2011/0282241 A1 | 11/2011 | Swayze et al. | |
| 2012/0024788 A1 | 2/2012 | Kelso et al. | |
| 2013/0130226 A1 | 5/2013 | Lim et al. | |
| 2013/0143226 A1 | 6/2013 | Hill et al. | |
| 2013/0280725 A1 | 10/2013 | Ismagilov et al. | |
| 2014/0248621 A1 * | 9/2014 | Collins | G01N 15/1031 435/6.12 |
| 2016/0033373 A1 | 2/2016 | Hill et al. | |

FOREIGN PATENT DOCUMENTS

| | | |
|---|---|---|
| EP | 1 880 671 A1 | 1/2008 |
| WO | WO 00/10682 A1 | 3/2000 |
| WO | WO 2005/066627 A1 | 7/2005 |
| WO | WO 2008/085052 A2 | 7/2008 |
| WO | WO 2009/075709 A1 | 6/2009 |

(Continued)

OTHER PUBLICATIONS

Homsey et al. "Development and validation of a low cost blood filtration element separating plasma from undiluted whole blood", Biomicrofluidics 6(1): 012804, 2012 (Year: 2012).*
Examination Report dated Feb. 7, 2014, for Australian Application No. AU 2011293832, 6 pages.
Examination Report dated Jul. 11, 2017, for Australian Application No. AU 2014236184, 4 pages.
Extended European Search Report dated Oct. 8, 2014, for European Application No. EP 11820329.8, 7 pages.
Extended European Search Report dated Oct. 18, 2016, for European Application No. EP 14768051.6, 7 pages.
Extended European Search Report dated Jul. 3, 2017, for European Application No. EP 14871438.9, 8 pages.

(Continued)

*Primary Examiner* — Emily A Cordas (57) ABSTRACT

The present invention provides systems, devices, kits, and methods for separating blood plasma or serum from whole blood. The present invention further provides systems, devices, and methods for separating a volume of blood plasma or serum from whole blood.

20 Claims, 6 Drawing Sheets

(56) References Cited

FOREIGN PATENT DOCUMENTS

WO    WO-2012027048 A2 *  3/2012   ......... A61B 5/15142

OTHER PUBLICATIONS

International Search Report and Written Opinion dated Apr. 17, 2015, for PCT/US2014/071763, 8 pages.
International Search Report and Written Opinion dated Aug. 19, 2014, for PCT/US2014/029440, 6 pages.
International Search Report and Written Opinion dated Jan. 31, 2012, for PCT/US2011/045167, 10 pages.
Examination Report dated Oct. 22, 2018, for Australian Application No. AU 2014368940, 3 pages.
Office Action dated Apr. 20, 2020, for Canadian Application No. 2,906,783, 3 pages.
Alfa Laval: "Alfa Laval -membrane filtration", Jan. 1, 2003 (Jan. 1, 2003), XP055707953, Retrieved from the Internet: URL:https://www.alfalaval.com/globalassets/documents/industries/pulp-and-paper/al-membranefiltration.pdf [retrieved on Jun. 23, 2020].
Examination Report dated Jun. 30, 2020, for Indian Patent Application No. 201617024409, 7 pages.
Lee et al., "High-throughput cell cycle synchronization using inertial forces in spiral microchannels", Lab on a Chip, vol. 11, No. 7, Jan. 1, 2011 (Jan. 1, 2011), p. 1359-1367.
Office Action dated Jul. 8, 2020, for European Application No. 14871438.9, 6 pages.
Stamatialis et al., "Medical applications of membranes: Drug delivery, artificial organs and tissue engineering", Journal of Membrane Science, Elsevier BV, NL, vol. 308, No. 1-2, Dec. 19, 2007 (Dec. 19, 2007), pp. 1-34.
Examination Report dated Sep. 8, 2020, for Australian Application No. AU 2020200643, 4 pages.

* cited by examiner

WHOLE BLOOD SEPARATION SAMPLING APPARATUS

CROSS-REFERENCES TO RELATED APPLICATIONS

This Application claims the benefit under 35 U.S.C. § 119(e) of U.S. Provisional Patent Application No. 61/919,526 filed Dec. 20, 2013 which is incorporated herein by reference in its entirety as if fully set forth herein.

STATEMENT REGARDING FEDERALLY SPONSORED RESEARCH OR DEVELOPMENT

This invention was made with government support under W31P4Q-11-C-0234 awarded by Defense Advanced Research Projects Agency (DARPA). The government has certain rights in the invention.

FIELD OF THE INVENTION

The present invention provides systems, devices, kits, and methods for separating blood plasma or serum from whole blood. In particular, the present invention provides systems, devices, and methods for separating a volume of blood plasma or serum from whole blood.

BACKGROUND OF THE INVENTION

Several up-stream processes are required before a complex biological fluid can be analyzed for analytes. The separation of plasma or serum is also a critical upstream process for the detection and diagnosis of infectious diseases. In a laboratory setting, the separation of plasma from whole blood is carried out by centrifugation of blood for 20 minutes at 3000 g. In doing so, the solid components of blood settle down in the sediment and the supernatant liquid consists of plasma. This protocol usually requires a trained technician to manually pipette out the supernatant for further analysis. While large scale automated sample preparation systems can eliminate the manual step, these instruments are expensive instrumentation, making them unsuitable for resource limited or point-of-care testing.

Methods have been designed to integrate the centrifugal blood separation with further downstream steps through a micro-fluidic platform. However, these methods work with an extremely limited volume of whole blood, require the use of an instrument to create the centrifugal force, are prone to clogging, and/or achieve only limited purity. The use of synthetic membranes to separate blood from plasma avoids some of the problems presented by centrifugation and microfluidics systems; however, devices are complex due to the need for multiple filtrations, and contain materials which retard the flow of blood into the filters.

The present invention seeks to provide for a body fluid collection and storage device as a dried sample providing for increased sample stability/longevity and protection from contamination or degradation.

The present invention provides systems, devices, kits, and methods for separating blood plasma from whole blood. In particular, the present invention provides systems, devices, and methods for separating a volume (e.g., fixed volume) of blood plasma or serum from blood cell component of whole blood.

Specifically, the claimed invention provides an apparatus that allows blood collection, separation and drying as well as storage in an enclosed cartridge, and uses a spiral membrane which allows lateral flow blood separation in a round, spiral form.

SUMMARY OF THE INVENTION

The present invention provides a single-use apparatus for blood collection and storage as a dried sample comprising structural components that form an interior circular chamber(s) containing a sample collection material(s), and a desiccant, the sample collection material being in fluid communication with a capillary tube or opening that extend to the exterior of the device and through which the user introduces the fluid to be collected. The all-in-one design of the device makes it ideally suited for collection of blood samples in the field, where conventional sample collection would be difficult.

An embodiment of the invention provides a device having a spiral filtering membrane that allows lateral flow blood separation. The spiral form of the membrane allows separation of components of blood by virtue of the lateral flow.

In some embodiments, the present invention provides a method of filtering blood plasma comprising: (a) providing: (i) a filter module, wherein the filter module comprises a filter membrane configured to allow lateral or horizontal flow; and (ii) a blood sample; (b) applying the blood sample to the filter membrane of the filter module; and (c) allowing the blood sample to flow laterally or horizontally through the filter membrane. In some embodiments, the filter module accommodates a fixed volume of blood sample.

DESCRIPTION OF EXEMPLARY EMBODIMENTS

The invention is directed to a fluid sampling device. In certain embodiments, the fluid being sampled is blood. The device contains one or more sampling materials suitable for collecting the body fluid. Such sample collecting materials can include, as non-limiting examples, filter paper or other solid support made from materials including nylon, polypropylene, polyester, rayon, cellulose, cellulose acetate, nitrocellulose, mixed cellulose ester, glass microfiber filters, cotton, quartz microfiber, polytetrafluoroethylene, polyvinylidene fluoride and the like. In some preferred embodiments of the invention, the sample collecting materials can be chemically treated to assist sample retention, test preparation, or increase sample longevity, amongst other things. Non-limiting examples include: to inactivate bacteria and/or viruses; to denature proteins; to lyse cells, to inactivate proteases, RNAses, DNAses and other enzymes, and/or to aid in sample preparation. In some preferred embodiments, the sampling material may be perforated or partitioned so as to provide the sampler or tester with readily separable pieces of sampling material.

In some embodiments of the invention, the collection material is placed on a sample collection material such as a filter having a spiral form.

In some preferred embodiments of the invention, the interior of the device contain a drying agent or desiccant to remove moisture from the sample. In further embodiments of the invention, the drying agent or desiccant is separated from the filter by a mesh-like barrier.

In certain embodiments, the interior of the device contains a barrier to calibrate the rate of drying of the sample. The barrier is made of materials such as filter paper, waxed paper, plastics with small holes, and is placed between the mesh-like barrier and desiccant.

In some preferred embodiments of the present invention, the device additionally comprises a lancet, needle, or other mechanism to puncture the skin in order to provide access to the particular body fluid.

In certain embodiments of the invention, the claimed device provides a small footprint for easy handling. In further embodiments of the invention, the device provides for fluid (whole blood) separation from a small sample (2-6 drops) and drying and storage for downstream testing. Additionally, the device displays low hemolysis of the blood sample onto the spiral membrane.

The present invention provides systems, devices, kits, and methods for separating blood plasma or serum from whole blood. In particular, the present invention provides systems, devices, and methods for separating a volume (e.g., fixed volume) of blood plasma or serum from whole blood. In some embodiments, the present invention provides systems and devices for separating blood plasma or serum from whole blood. In some embodiments, devices separate blood plasma or serum from other blood components (e.g., blood cells). In some embodiments, the present invention provides a filter element. In some embodiments, whole blood (e.g., unfiltered) is added to a filter element, and the blood is filtered (e.g., by capillary action, by gravity, etc.) through the filter element using lateral flow. In some embodiments of the device, certain analytes might be added to the filter element as an internal standard.

An embodiment of the invention is directed to a method of filtering blood plasma or serum comprising: a) providing: i) a filter module, wherein said filter module comprises a filter configured to allow passage of blood plasma or serum but not other blood components; and ii) a blood sample; b) applying said blood sample to said filter of said filter module; and c) filtering said blood plasma or serum through said filter.

Another embodiment of the invention is directed to a device for separating plasma or serum from whole blood comprising a) a filter module, wherein said filter module comprises a filter configured to allow passage of blood plasma or serum but not other blood components.

In some embodiments, the present invention provides a filter element.

In some embodiments, one or more blood components (e.g., cellular components) move more slowly through the filter element than blood plasma.

Figure 1:
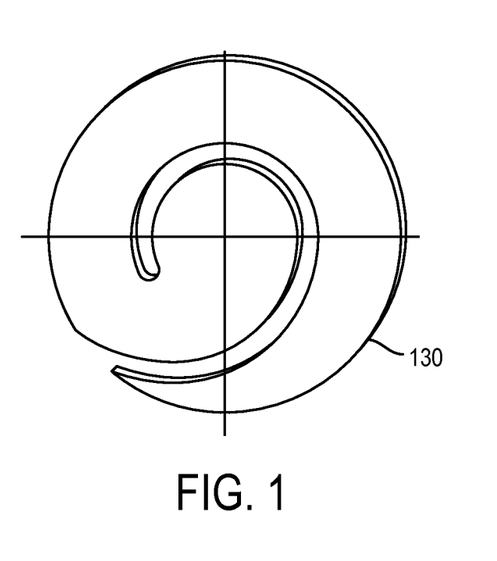
FIG. 1 shows a spiral filter membrane in accordance with an embodiment of the invention.

In some embodiments, blood components other than plasma (e.g., cellular components) are unable to move through the filter element. In some embodiments, blood plasma rapidly (e.g., more rapidly than other blood components) advances through the filter element. In some embodiments, the filter element comprises a filter capable of separating blood plasma from other blood components based on capillarity. In some embodiments, the filter is a spiral membrane. In certain embodiments, the filter is a circular membrane. A spiral-shaped membrane is shown in accordance with an embodiment of the invention is shown in FIG. 1.

The advantages/benefits for using a spiral membrane include a small footprint that fits into a cartridge (easy handling). Additionally a spiral membrane allows fluid (whole blood) separation from a small sample (2-6 drops) and drying and storage for downstream testing. Furthermore, the use of a spiral membrane reduces the level of hemolysis of the sample blood during movement on to the membrane by virtue of the use of lateral movement of the sample on to the membrane.

The device of the present invention presents advantages/benefits compared to the existing blood separation devices. These advantages include separating cells such as red blood cells and white blood cells from whole blood; use of a drying agent (desiccant) separated from the sampling membrane by plastic mesh with air holes allowing rapid drying; and the ability to calibrate drying rate and thus control resulting sample area.

Figure 2:
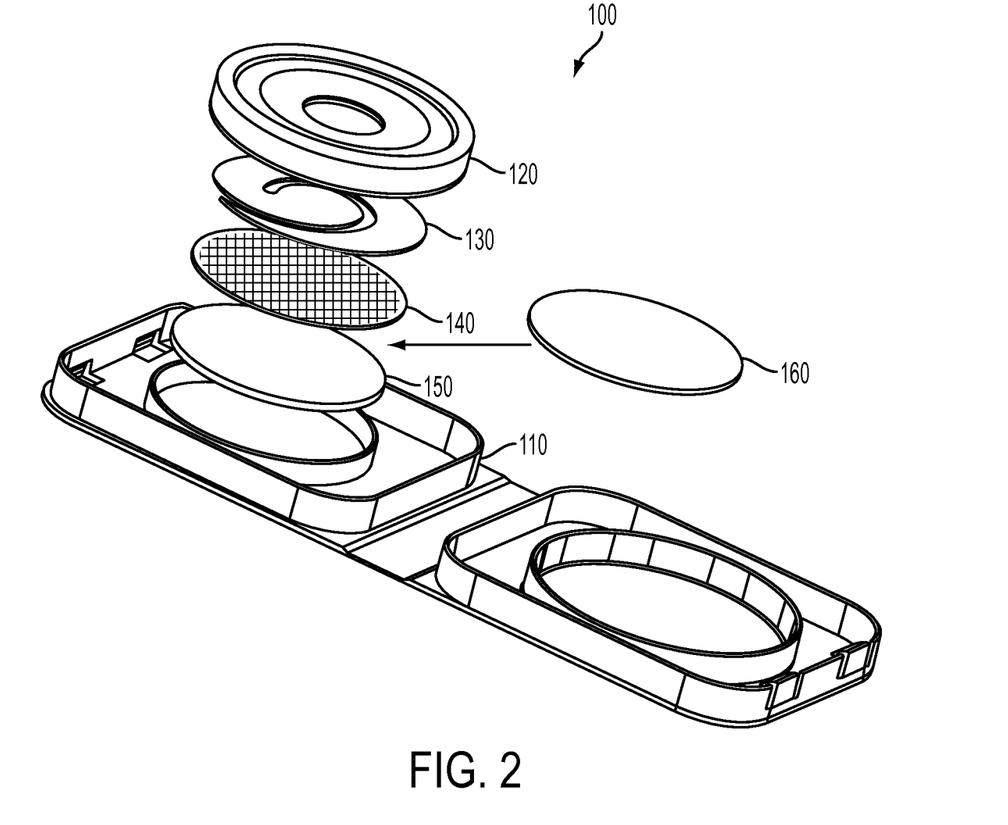
FIG. 2 shows a fluid collection device in accordance with an embodiment of the invention.

As set forth in FIG. 2, the device of the claimed invention 100 comprises several components. A moisture-tight cartridge 110 is provided. Inside the cartridge 110, the applicator 120, sampling membrane 130, mesh barrier 140 and desiccant 150 are arranged as shown in FIG. 2. The mesh barrier 140 is arranged between the desiccant 150 and the sampling membrane 130 to prevent contact between the desiccant and the sampling membrane while still furthering the drying process. In certain embodiments, an additional barrier 160 is inserted between the mesh barrier 140 and the desiccant 150. The barrier 160 calibrates the rate of drying of the sample and provides an accurate reading of the component being measured.

Working Examples

Multiple designs were examined in an attempt to identify an ideal form that could take advantage of the existing HEMASPOT™ platform, while providing enough surface area and length to allow the plasma/serum to separate from red blood cells, while also remaining concentrated enough to allow easy isolation of sufficient material for analytical work. While a straight line for the blood to wick down is the most obvious design for the separation process, a straight line would not fit into the HEMASPOT™ platform while a circular design would be compact and fit well.

After a number of design trials were investigated, all designed to fit under the HEMASPOT™ applicator and above the HEMASPOT™ desiccant, a final spiral design was identified that could provide the area needed for up to 150 µL of whole blood and the length required to allow separation of the plasma or serum component from the whole blood.

Trials were performed to identify the area of the material the red blood cells would occupy. With addition of 50, 75 and 100 µL of whole blood (WB), the average red blood cell (RBC) area was found to be 4.0 $mm^{-2}/\mu L$ WB. For an estimated 80 to 100 µL of WB from a finger stick, the area occupied by RBC's would be between 320 and 400 $mm^{-2}$.

To this end, spiral forms were crafted (see FIGS. 1 & 2) with a center portion ranging from approximately 12-14 mm diameter, comprising up to 154 mm$^{-2}$ area. This area is enough to hold the RBC's from 40 μL of WB with an average hematocrit (HCT). With the spiral arm being approximately 8 mm in width around the center, RBC's would be expected to move only a quarter of the circumference around the spiral. Plasma or serum would occupy the remainder of the spiral arm.

Figure 3A:
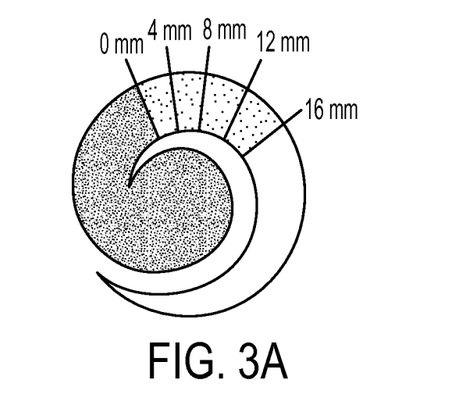
FIG. 3A shows the use of the spiral filter in accordance with an embodiment of the invention.
Figure 3B:
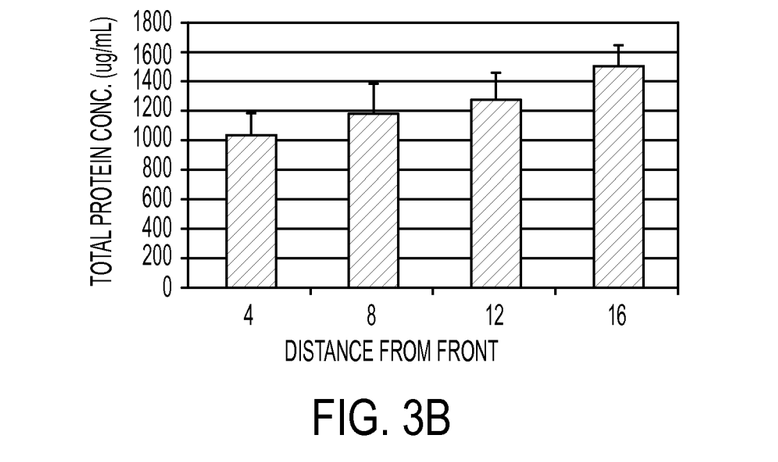
FIG. 3B shows the results of the use of a spiral filter in accordance with an embodiment of the invention.

In an experimental trial, a blood sample was placed on a spiral membrane at a location "0" as set forth in FIG. 3A. 4 mm punches were taken from the plasma portion around the spiral to analyze for any chromatographic effect the filter material might have on total protein. A picture of this arrangement is provided in FIG. 3A. The results of the protein analysis of each of the four punches from two trials are provided in FIG. 3B. From FIG. 3B, a chromatographic effect of total protein can be seen as the punch location moves away from the red blood cell front. The farther the location of the punch sample, the greater the protein concentration due to the presence of increasing amounts of plasma and serum at locations on the filter farther away from the sampling site. Thus, there is a greater amount of protein at a distance of 16 mm from the sampling site than at 8 mm.

Figure 4A:
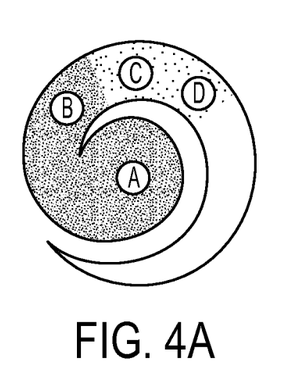
FIG. 4A shows the use of the spiral filter in accordance with an embodiment of the invention.
Figure 4B:
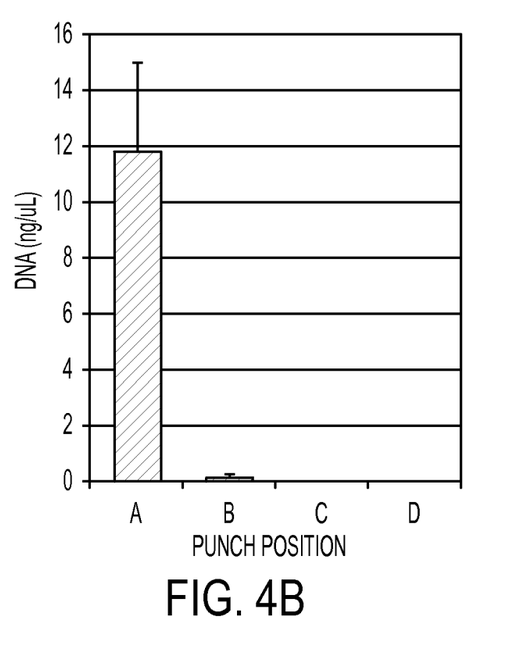
FIGS. 4B to 4D shows the results of the use of a spiral filter in accordance with an embodiment of the invention.
Figure 4C:
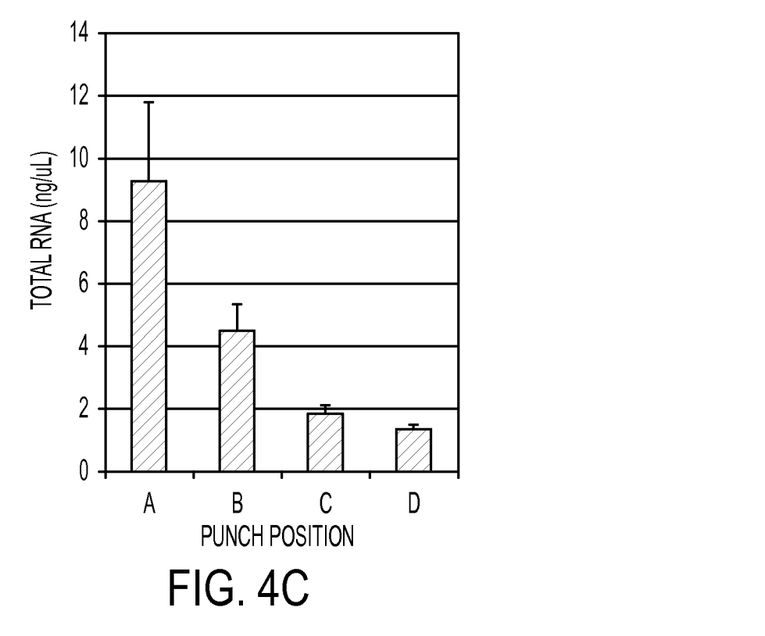
Figure 4D:
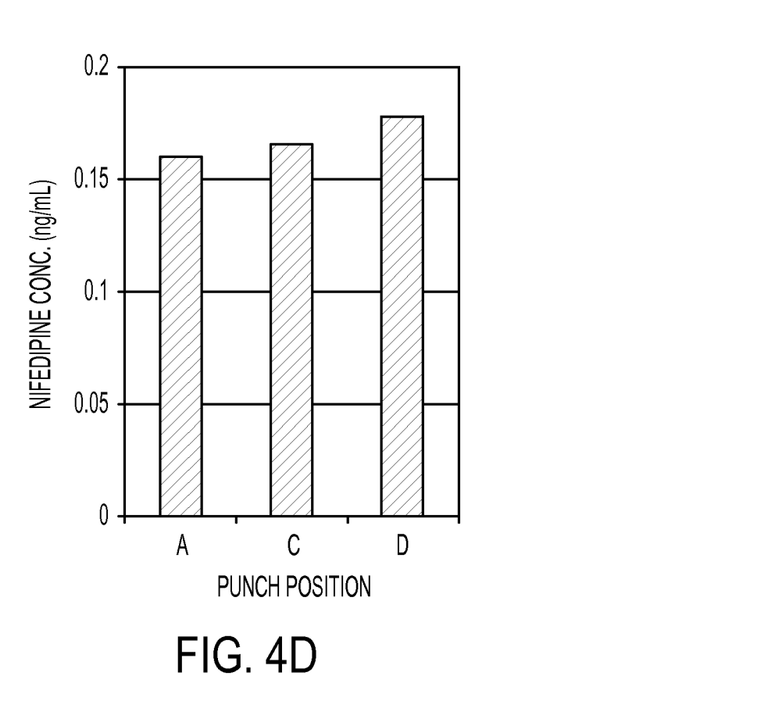

As shown in FIGS. 4A to 4C, fresh whole human blood was applied to the spiral form and dried. Punches were removed as indicated (FIG. 4A) and extracted. DNA was isolated using DNAZOL® standard methods and measured by PICOGREEN® fluorescence (FIG. 4B). RNA was isolated by TRIZOL® methods and analyzed by absorbance at 260 and 280 nm (FIG. 4C). A small molecule, nifedipine, was analyzed by LC-MS/MS methods (FIG. 4D). As shown in FIG. 4B, the greatest concentration of DNA is located at the site where the sample is introduced onto the filter. Similarly, the concentration of RNA is greatest at the site where the sample is introduced onto the filter. The RNA and DNA concentrations dramatically decrease as the distance of the punch location increases from the sampling site.

Figure 5A:
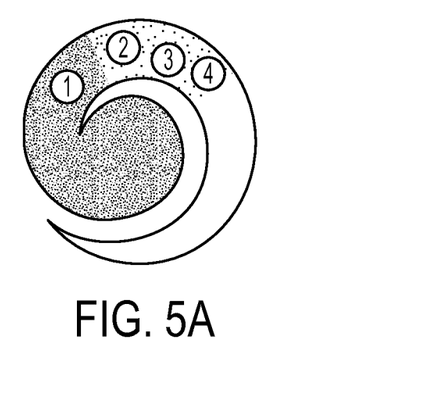
FIG. 5A shows the use of the spiral filter in accordance with an embodiment of the invention.
Figure 5B:
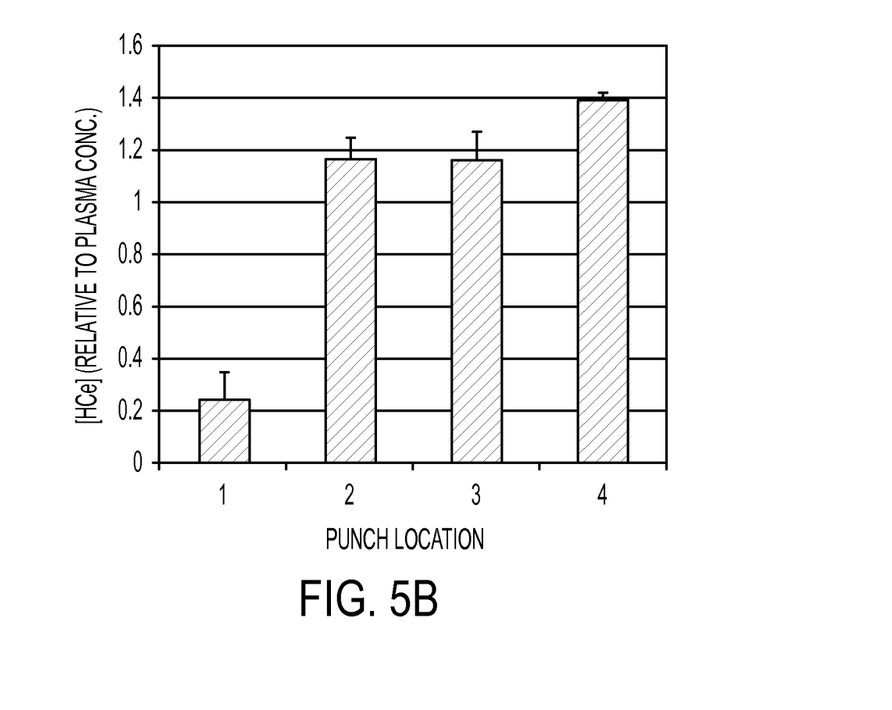
FIG. 5B shows the results of the use of a spiral filter in accordance with an embodiment of the invention.

Fresh whole human blood was applied to spiral membrane and dried (FIG. 5A). Punches were removed as indicated (FIG. 5A) and extracted. Homocysteine levels were measured by LC-MS/MS methods (FIG. 5B). As seen in FIG. 5B, there is a greater amount of homocysteine at a punch location 4, i.e., the location that is farthest from the sampling site than at punch location 1, i.e., the location that is closest to the sampling site. This result proves that homocysteine levels are higher in the plasma areas than in the cell areas.

Embodiments of the invention provide the ability to sample specific components of whole blood in an efficient manner in a single sampling. The present invention provides a time-saving and space saving device and method to sample whole blood using minimal amounts of sample (2-6 drops).

Although particular embodiments of the invention have been described, other embodiments are within the scope of the following claims. For example, the actions recited in the claims can be performed in a different order and still achieve desirable results.

What is claimed is:

1. A method of separating non-cellular components of a sample of blood from the cellular components of the sample of blood, the method comprising the steps of:
   providing a sampling membrane configured to receive and contain the sample of blood, the sampling membrane configured to retard a movement of the cellular components relative to a movement of the non-cellular components; and
   applying the sample of blood to a central portion of the sampling membrane such that the sampling membrane retards the movement of the cellular components relative to the movement of the non-cellular components and includes, after a predefined period of time from receiving the blood, a plurality of testing sites that each provide different concentrations of the cellular components and the non-cellular components.

2. The method of claim 1, wherein the sampling membrane is configured to receive and contain a fixed volume of the sample of blood.

3. The method of claim 1, wherein the sampling membrane is disposable within a cartridge having an interior chamber that is configured to house the sampling membrane.

4. A device for separating non-cellular components of a sample of blood from cellular components of the sample of blood, the device comprising:
   a sampling membrane configured to receive and contain the sample of blood, the sampling membrane configured to retard a movement of the cellular components relative to a movement of the non-cellular components such that the sampling membrane, after a predefined period of time from receiving the sample of blood, includes a plurality of testing sites that each provide different concentrations of the cellular components and the non-cellular components.

5. The device of claim 4, wherein the sampling membrane is configured to receive and contain a fixed volume of the sample of blood.

6. The device of claim 4, further comprising a drying agent disposable beneath the sampling membrane, the drying agent configured to remove moisture from the sample of blood after the sampling membrane receives the sample of blood.

7. The device of claim 6, further comprising a mesh-like barrier disposable between the sampling membrane and the drying agent, the mesh-like barrier configured to separate the sampling membrane from the drying agent.

8. The device of claim 7, further comprising a barrier disposable between the mesh-like barrier and the drying agent, the barrier configured to control a rate of moisture being removed by the drying agent from the sample of blood.

9. The device of claim 4, further comprising a cartridge having an interior chamber configured to house the sampling membrane.

10. The device of claim 4, wherein the sampling membrane is formed of at least one of the following: nylon, polypropylene, polyester, rayon, cellulose, cellulose acetate, nitrocellulose, mixed cellulose ester, glass microfiber filters, cotton, quartz microfiber, polytetrafluoroethylene, or polyvinylidene fluoride.

11. The device of claim 4, wherein the sampling membrane is formed of a material that has been chemically treated to assist with at least one of the following: sample retention, test preparation, or increased sample longevity.

12. The device of claim 4, wherein the sampling membrane is perforated such that the sampling membrane can be readily separated into one or more portions.

13. The device of claim 4, wherein the sampling membrane includes:
   a center portion with a diameter of approximately 12-14 millimeters (mm); and
   a spiral arm with a maximum width of approximately 8 mm, the spiral arm having a first end connected to the center portion and a tapering portion that extends around a portion of a perimeter of the center portion and tapering to a second end of the spiral arm.

14. The device of claim 4, further comprising a moisture-tight cartridge having an interior chamber configured to house the sampling membrane, the moisture-tight cartridge configured to provide a moisture-tight barrier between the sampling membrane and an external environment.

15. The device of claim 4, wherein the plurality of testing sites includes:
- a first testing site located on a center portion of the sampling membrane, the first testing site including a first concentration of the cellular components and a first concentration of the non-cellular components; and
- a second testing site located a first distance along a spiral arm of the sampling membrane, the second testing site including a second concentration of the cellular components that is less than the first concentration of the cellular components and a second concentration of the non-cellular components that is greater than the first concentration of the non-cellular components.

16. The device of claim 15, wherein the plurality of testing sites further includes a third testing site located a second distance along the spiral arm that is greater than the first distance, the third testing site including:
- a third concentration of the cellular components that is less than the first concentration of the cellular components and the second concentration of the cellular components; and
- a third concentration of the non-cellular components that is greater than the first concentration of the non-cellular components and the second concentration of the non-cellular components.

17. The device of claim 7, further comprising an applicator including a center opening, the applicator disposable over the sampling membrane such that a center portion of the sampling membrane is exposed for receiving the sample of blood, the applicator having an outer diameter greater than the outer diameter of the sampling membrane.

18. The device of claim 4, wherein the cellular components include at least one of red blood cells or white blood cells, and the non-cellular components include at least one of plasma or serum.

19. The device of claim 4, wherein the sampling membrane is spiral-shaped.

20. A system, comprising:
- the device of claim 4; and
- a puncturing mechanism configured to puncture a skin of a subject to provide access to the sample of blood for being received on the sampling membrane.

* * * * *